(12) United States Patent
Baets et al.

(10) Patent No.: US 10,266,856 B2
(45) Date of Patent: *Apr. 23, 2019

(54) METHOD FOR THE PREPARATION OF LACTIC ACID

(71) Applicant: PURAC BIOCHEM BV, Gorinchem (NL)

(72) Inventors: Peter Johannes Marie Baets, Spijk (NL); David Sanchez Garcia, Rotterdam (NL); Willem Jacob Groot, Dordrecht (NL); André Banier De Haan, Best (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/329,179

(22) PCT Filed: Jul. 28, 2015

(86) PCT No.: PCT/EP2015/067258
§ 371 (c)(1),
(2) Date: Jan. 25, 2017

(87) PCT Pub. No.: WO2016/016233
PCT Pub. Date: Feb. 4, 2016

(65) Prior Publication Data
US 2017/0218408 A1    Aug. 3, 2017

(30) Foreign Application Priority Data

Jul. 28, 2014 (EP) ..................... 14178812
Jul. 28, 2014 (EP) ..................... 14178813

(51) Int. Cl.
*C12P 7/56* (2006.01)
*D21C 1/06* (2006.01)

(52) U.S. Cl.
CPC ............... *C12P 7/56* (2013.01); *D21C 1/06* (2013.01); *C12P 2201/00* (2013.01); *C12P 2203/00* (2013.01); *Y02P 20/582* (2015.11)

(58) Field of Classification Search
None
See application file for complete search history.

(56) References Cited

U.S. PATENT DOCUMENTS

| 6,509,179 | B1 | 1/2003 | Veldhuis-Stribos et al. |
| 6,630,603 | B1 | 10/2003 | Van Breugel et al. |
| 2013/0122554 | A1 | 5/2013 | Ueyama et al. |
| 2013/0210084 | A1* | 8/2013 | Guerini ............... C12P 19/14 435/99 |
| 2013/0236933 | A1 | 9/2013 | Huang et al. |
| 2017/0292133 | A1* | 10/2017 | Baets ............... D21C 3/02 |

FOREIGN PATENT DOCUMENTS

| GB | 706686 A | 4/1954 |
| GB | 812832 A | 5/1959 |
| JP | 2006-101829 A | 4/2006 |
| JP | 2008-271962 A | 11/2008 |
| NL | 1013265 C2 | 4/2001 |
| NL | 1013682 C2 | 5/2001 |
| WO | 00/17378 A2 | 3/2000 |
| WO | 01/32715 A1 | 5/2001 |
| WO | 03/095659 A1 | 11/2003 |
| WO | 2005/074647 A2 | 8/2005 |
| WO | 2005/123647 A1 | 12/2005 |
| WO | 2008/148131 A1 | 12/2008 |
| WO | 2009/025547 A1 | 2/2009 |
| WO | 2011/035027 A2 | 3/2011 |
| WO | 2011/095631 A1 | 8/2011 |
| WO | 2013/062407 A1 | 5/2013 |
| WO | 2013/093028 A1 | 6/2013 |
| WO | 2013/117687 A1 | 8/2013 |

OTHER PUBLICATIONS

Garde et al. Lactic acid production from wheat straw hemicellulose hydrolysate by Lactobacillus pentosus and Lactobacillus brevis., Bioresource Technology (2002), 81: 217-223.*
Oct. 5, 2015 International Search Report issued in International Patent Application No. PCT/EP2015/067258.
Oct. 5, 2015 Written Opinion issued in International Patent Application No. PCT/EP2015/067258.
Vincent S. Chang et al; "Fundamental Factors Affecting Biomass Enzymatic Reactivity;" Applied Biochemistry and Biotechnology; vol. 84-86; pp. 5-37.
Fanran Kong et al; "Effects of Cell-Wall Acetate, Xylan Backbone, and Lignin on Enzymatic Hydrolysis of Aspen Wood;" Applied Biochemistry and Biotechnology; Mar. 1, 1992; vol. 34-35; pp. 23-35.
Ann Herlevich Brennan et al; "High Temperature Acid Hydrolysis of Biomass Using an Engineering-Scale Plug Flow Reactor: Results of Low Solids Testing;" Biotechnology and Bioengineering Symp.; 1986; No. 17; pp. 53-70.

(Continued)

*Primary Examiner* — Iqbal H Chowdhury
(74) *Attorney, Agent, or Firm* — Oliff PLC (57) ABSTRACT

A method for preparing a fermentation product including lactic acid, the method including: a) treating lignocellulosic material with caustic magnesium salt in the presence of water to provide treated aqueous lignocellulosic material; b) saccharifying the treated aqueous lignocellulosic material in the presence of a hydrolytic enzyme to provide a saccharified aqueous lignocellulosic material comprising fermentable carbohydrate and a solid lignocellulosic fraction; c) simultaneously with step b), fermenting the saccharified aqueous lignocellulosic material in the presence of both a lactic acid forming microorganism and caustic magnesium salt to provide an aqueous fermentation broth comprising magnesium lactate and a solid lignocellulosic fraction; d) recovering magnesium lactate from the broth, wherein the saccharification and the fermentation are carried out simultaneously.

25 Claims, 1 Drawing Sheet

(56) References Cited

OTHER PUBLICATIONS

Alireza Esteghlalian et al; "Modeling and Optimization of the Dilute-Sulfuric-Acid Pretreatment of Corn Stover, Poplar and Switchgrass;" Bioresource Technology; 1997; 59; pp. 129-136.

David J. Fox et al; "Comparison of Alkali and Steam (Acid) Pretreatments of Lignocellulosic Materials to Increase Enzymic Susceptibility: Evaluation under Optimized Pretreatment Conditions;" J. Chem. Tech. Biotechnol.; 1989; vol. 44; pp. 135-146.

N.D. Hinman et al; "Preliminary Estimate of the Cost of Ethanol Production for SSF Technology;" Applied Biochemistry and Biotechnology; 1992; vol. 34/35; pp. 639-649.

Sehoon Kim et al; "Effect of structural features on enzyme digestibility of corn stover;" Bioresource Technology; 2006; vol. 97; pp. 583-591.

Douglas G. MacDonald et al; "Alkali Treatment of Corn Stover to Improve Sugar Production by Enzymatic Hydrosis;" Biotechnology and Bioengineering; 1983; vol. 25; pp. 2067-2076.

* cited by examiner

METHOD FOR THE PREPARATION OF LACTIC ACID

FIELD OF THE INVENTION

The present invention is directed to a method for preparing lactic acid from lignocellulosic materials. More particularly, the present invention is directed to a method in which lignocellulosic material, which has been pre-treated with a caustic magnesium salt, is subjected to simultaneous saccharification and fermentation to derive magnesium lactate, from which salt lactic acid may be derived by direct acidulation.

BACKGROUND OF THE INVENTION

Lactic acid is widely used in the food, pharmaceutical, plastics and textile industries. It is also used as a source of lactic acid polymers which find utility as biodegradable plastics and of which the physical properties can be controlled by adjusting the proportions of the L(+)- and D(−)-lactides.

Lactic acid can be produced by fermentation but the economics of such production is strongly dependent upon the cost of the raw materials. It is, for instance, very expensive when refined sugars and starch are used as the fermentation feedstock. Lignocellulosic biomass, which has no competing food value, is a lower-cost, alternative feedstock having wide availability and the potential to be sourced sustainably. However, there is still a need in the art to improve the commercial scale fermentation of lignocellulosic biomass for lactic acid production.

The present invention is concerned in part with methods of treatment of lignocellulosic materials which render the materials more amenable to biologically mediated transformations. More particularly, it is concerned with methods of treatment which render the lignocellulosic materials more amenable to at least one of: enzymatic hydrolysis of carbohydrate components to sugars by saccharolytic enzymes present in the pretreated biomass; microbial hydrolysis by microorganisms capable of the fermentation of hexose sugars such as glucose, mannose, and galactose; and, microbial hydrolysis by microorganisms capable of the fermentation of pentose sugars such as xylose and arabinose.

Approximately 90% of the dry weight of most plant materials is stored in the form of cellulose, hemicellulose, lignin and pectin, with the remainder being constituted by proteins, ash and extractives such as non-structural sugars, nitrogenous materials, chlorophyll and waxes.

Cellulose is the main structural constituent in plant cell walls. It exists mainly in a crystalline form and is typically found in an organized fibrous structure: the linear cellulose polymer consists of D-glucose subunits linked to each other by $\beta$-(1,4)-glycosidic bonds; cellobiose is the repeat unit established through this linkage, and it constitutes cellulose chains; in turn, the long-chain cellulose polymers are linked together by hydrogen and van der Waals bonds, which cause the cellulose to be packed into microfibrils; and, hemicelluloses and lignin then cover said microfibrils. Fermentable D-glucose can be produced through the action of either acid or enzymes breaking the $\beta$-(1,4)-glycosidic linkages and the amorphous form of cellulose is more susceptible to such enzymatic degradation. However, high cellulose crystallinity, low accessible surface area, protection by lignin, and sheathing by hemicellulose all contribute to the resistance of cellulose in lignocellulosic biomass to hydrolysis.

Hemicellulose is mainly differentiated from cellulose in that hemicellulose has branches with short lateral chains consisting of different sugars. These monosaccharides include pentoses (xylose, rhamnose, and arabinose), hexoses (glucose, mannose, and galactose), and uronic acids (e.g., 4-o-methylglucuronic, D-glucuronic, and D-galactouronic acids). The backbone of hemicellulose is either a homopolymer or a heteropolymer with short branches linked by $\beta$-(1,4)-glycosidic bonds and occasionally $\beta$-(1,3)-glycosidic bonds. Also, hemicelluloses can have some degree of acetylation.

Lignin is a complex, three-dimensional polymer constituted by phenylpropanoid subunits linked together by a variety of ether and carbon-carbon bonds. Lignin is intimately interlaced with hemicelluloses in the plant cell wall forming a matrix to cover the crystalline cellulose microfibrils. Whilst it imparts structural support and impermeability to the cell wall, its presence concomitantly provides a protective barrier that prevents plant cell destruction by fungi and those bacteria necessary for the conversion of biomass to organic acids. Lignin's aromatic nature and complex structure make lignin degradation very difficult. Both lignin and lignin-derived compounds have a detrimental effect on the enzymatic hydrolysis of biomass because they physically hinder the accessibility of cellulases; they also bind cellulases and lead to their inactivation.

Pre-treatment methods to break down lignin are thus essential for the effective enzymatic and microbial hydrolysis of lignocellulose and thus for the conversion of lignocellulose into organic acids such as lactic acid, succinic acid and acetic acid. Known pre-treatment methods can be roughly divided into different categories: physical (milling and grinding), physicochemical (steam pre-treatment/autohydrolysis, hydro-thermolysis, and wet oxidation), chemical (alkali, dilute acid, oxidizing agents, and organic solvents), biological, electrical, or a combination of these. The present invention is concerned with a chemical pre-treatment process utilizing an alkaline agent.

Compared with acid pre-treatment processes, alkaline processes are considered to cause less sugar degradation, and many of the caustic salts can be recovered and/or regenerated. Kong et al. *Effects of cell-wall acetate, xylan backbone, and lignin on enzymatic hydrolysis of aspen wood*, Appl. Biochem. Biotechnol. 1992, 34/35, 23-35 reported that alkalis remove acetyl groups from hemicellulose (mainly xylan), thereby reducing the steric hindrance of hydrolytic enzymes and greatly enhancing carbohydrate digestibility.

Historically, sodium, potassium, calcium, and ammonium hydroxides have been preferred as alkaline pre-treatment agents and, of these, sodium hydroxide has been the most studied, as documented in, for instance: Fox, D. J et al., *Comparison of alkali and steam (acid) pretreatments of lignocellulosic materials to increase enzymic susceptibility: Evaluation under optimized pretreatment conditions* J. Chem. Tech. Biotech. 1989, 44, 135-146; and, MacDonald, D. G. et al. *Alkali treatment of corn stover to improve sugar production by enzymatic hydrolysis* Biotechnol. Bioeng. 1983, 25, 2067-2076.

Calcium hydroxide (slake lime) has also found utility as a pre-treatment agent, mainly on account of the facts that it is relatively inexpensive (per kilogram) and that it is possible to recover calcium from an aqueous reaction system as insoluble calcium carbonate by neutralizing it with inexpensive carbon dioxide; the calcium hydroxide can subsequently be regenerated using established lime kiln technology. Lime pre-treatment does however tend to increase the crystallinity index of the pre-treated lignocellulosic biomass. Whilst this may not have an effect on ultimate sugar yields from enzymatic hydrolysis, the crystallinity significantly affects initial hydrolysis rates as reported in Chang et al. *Fundamental factors affecting biomass enzymatic reactivity*, Appl. Biochem. Biotechnol. 2000, 84-86, 5-37.

Further as reported by Kim et al. *Effect of structural features on enzyme digestibility of corn stover*, Bioresour. Technol. 2006, 97, 583-591, the delignification of a given lignocellulosic material with calcium hydroxide can vary significantly with oxidative conditions and temperature. This brings into question the efficacy of calcium hydroxide in industrial processes where oxidative conditions cannot easily be moderated and where the lignocellulosic feedstock may be derived from more than one plant material or source, noting that the composition of lignin, hemicellulose and cellulose can vary from one plant species to another and, for a single plant type may vary with age and stage of growth.

WO2013/062407 (Wageningen University et al.) describes a process for the conversion of lignocellulosic material into an organic acid comprising an alkaline pre-treatment step and a fermentation step. Whilst the document purports magnesium oxide or magnesium hydroxide could be used in the alkaline pre-treatment step, this is not exemplified. Rather this document only demonstrates the use of calcium oxide or calcium hydroxide in a pre-treatment step which occurs at a temperature of from 20° to 115° C. For the purposes of achieving water balance in the process, the liquid phase obtained in the fermentation step must be recycled to the alkaline pre-treatment and/or the fermentation step.

STATEMENT OF THE INVENTION

In accordance with a first aspect of the present invention there is provided a method for producing a fermentation product comprising lactic acid from lignocellulosic material, said method comprising: a) treating a lignocellulosic material with an alkaline agent in the presence of water to provide a treated aqueous lignocellulosic material, said alkaline agent comprising a caustic magnesium salt; b) saccharifying the treated aqueous lignocellulosic material in the presence of a hydrolytic enzyme to provide a saccharified aqueous lignocellulosic material comprising fermentable carbohydrate and a solid lignocellulosic fraction; c) fermenting the saccharified aqueous lignocellulosic material in the presence of a lactic acid forming microorganism and in the presence of a caustic magnesium salt to provide an aqueous fermentation broth comprising magnesium lactate and a solid lignocellulosic fraction; and, d) recovering lactic acid and/or a lactate salt from said aqueous fermentation broth, wherein said saccharification and said fermentation are carried out simultaneously.

The solid lignocellulosic fraction derived from the simultaneous saccharification and fermentation steps comprises unhydrolyzed cellulose and hemicellulose and undissolved lignin fractions.

In an important embodiment, step a) of the above defined method comprises: i) providing a lignocellulosic material, which may optionally have been subjected to one or more of pre-extraction, acid hydrolysis and mechanical comminution; ii) mixing said lignocellulosic material with said alkaline agent in the presence of water to form a reaction mixture having a solids content; and, iii) heating said reaction mixture such that said solids are held at a temperature of from 130° C. to 250° C. for a time period of from 1 minute to 600 minutes.

Preferably, the caustic magnesium salt employed in step a) and step c) of the defined methods is independently selected from at least one of MgO, $Mg(OH)_2$, $MgCO_3$ and $Mg(HCO_3)_2$; the use of at least one of MgO and $Mg(OH)_2$ in step a) is particularly preferred.

Without being bound by theory, it is contended that the performance of the pre-treatment step a) at an elevated temperature facilitates the subsequent saccharification and fermentation of the lignocellulosic material by performing at least one of: efficiently degrading lignin; increasing the porosity of the lignocellulosic materials; eliminating non-productive enzyme adsorption sites; increasing enzymatic and/or microbial access to cellulose and hemicellulose; and, reducing the crystallinity of the cellulose; minimizing the degradation or loss of carbohydrate; and, minimizing the formation of by-products that are inhibitory to the subsequent saccharification and fermentation processes.

The use of divalent magnesium ions in the simultaneous saccharification and fermentation [b) and c)] has been found to be more productive—to result in higher titres—than the corresponding steps performed with monovalent ions.

In accordance with an important embodiment of the invention, the above defined method is used for preparing lactic acid; specifically the method steps of this embodiment comprise: a) treating a lignocellulosic material with an alkaline agent in the presence of water to provide a treated aqueous lignocellulosic material, said alkaline agent comprising a caustic magnesium salt; b) saccharifying the treated aqueous lignocellulosic material in the presence of a hydrolytic enzyme to provide a saccharified aqueous lignocellulosic material comprising fermentable carbohydrate and a solid lignocellulosic fraction; c) fermenting the saccharified aqueous lignocellulosic material in the presence of a lactic acid forming microorganism and in the presence of a caustic magnesium salt to provide an aqueous fermentation broth comprising magnesium lactate and a solid lignocellulosic fraction; d) recovering magnesium lactate from said aqueous fermentation broth; e) providing a feed comprising hydrogen chloride, said feed being either an aqueous solution comprising hydrogen chloride or a gas feed comprising gaseous hydrogen chloride; and, f) acidifying the magnesium lactate to lactic acid by bringing said magnesium lactate into contact with said feed comprising hydrogen chloride, thereby forming a liquid effluent comprising lactic acid and magnesium chloride. The magnesium chloride so-derived in recited step f) can easily be recovered and re-used.

Preferably, this process for producing lactic acid is characterized in that it further comprises the step(s): g) separation of lignin from the liquid effluent product of step f); and, preferably, h) separation of the lactic acid and magnesium chloride present in the liquid effluent product of step g) to obtain a lactic acid product stream and a magnesium chloride solution or suspension. In an embodiment, the separation step h) should comprise a lactic acid extraction step.

The separated magnesium chloride solution or suspension obtained in step h) may be subjected to a temperature of at least 300° C., to cause the thermal hydrolysis of the salt to solid magnesium oxide and gaseous hydrogen chloride. By performing this hydrolysis, the magnesium oxide derived may be used directly in at least one of step a) and step c) or, alternatively, may be used as a precursor for an alternative caustic magnesium salt used in at least one of step a) and step c); the magnesium oxide may, for instance, be slaked to provide $Mg(OH)_2$ for at least one of these steps. Analogously, that acidulation feed comprising hydrogen chloride which is used in step e) of the present invention may be at least partially derived from gaseous hydrogen chloride obtained from the thermal decomposition of the magnesium chloride.

The performance of a thermal hydrolysis step thus enables the recycling of important reactants within the recited process. It is also possible to mitigate the energy costs of the recited process by exchanging the heat stored in the products of the thermal hydrolysis.

Definitions

For the purposes of the instant description "an alkaline agent comprising a caustic magnesium salt" is also referred to as "magnesium-containing alkaline agent", or simply as "alkaline agent". The alkaline agent may be added to the lignocellulosic material in solid form, in the form of an aqueous solution or in the form of an aqueous slurry (e.g. having the caustic magnesium salt partially dissolved in water and partially in solid form).

The alkaline agent may comprise up to 50 wt. %, for example up to 20 wt. %, based on the dry weight of the alkaline agent, of one or more caustic salts other than a caustic magnesium salt, such as a caustic sodium salt, a caustic potassium salt, caustic calcium salt and/or a caustic ammonium salt. Specific examples of supplementary caustic salts include $Ba(OH)_2$, NaOH, $Na_2CO_3$, $NaHCO_3$, KOH, $K_2CO_3$, $KHCO_3$, CaO, $Ca(OH)_2$, $CaCO_3$, $Ca(HCO_3)_2$, $NH_4OH$, $(NH_4)_2CO_3$, and $(NH_4)$ $HCO_3$. It is however preferred the alkaline agent comprises more than 90 wt. %, preferably more than 95 wt. % and more preferably more than 98 wt. %, based on the dry weight of the alkaline agent, of caustic magnesium salt. In particular, the alkaline agent may consist solely of caustic magnesium salt. For example, the alkaline agent may consist of MgO and/or $Mg(OH)_2$.

Particle size measurements as given herein may be measured by laser light scattering using a well-known particle size analyzer such as CILAS 1064 instrument, available from Compagnie Industrielle des Lasers. Further standard techniques for analyzing particles sizes in the sub-millimeter range include the use of standard sieve shaker, microscopy and laser diffraction; these may equally be employed herein.

Where stated herein, the "solids content" or "dry weight" of the lignocellulosic material is determined by heating that material in air at 105° C. to a constant weight, in accordance with ASTM E1756-08.

For the purpose of this specification, the length of time the aqueous phase remains in the alkaline hydrolysis reactor is determined simply by dividing the working volume of the reactor by the volumetric mixture or slurry flow feed rate to the reactor. The length of time the unhydrolyzed solids are retained in the hydrolysis reactor is determined based on the solids concentration in the feed, at the exit and within the hydrolysis reactor, as is known in the art. The solids retention time may equally be calculated by using a tracer compound that binds to the solids.

The term "lactic acid" in this application refers to 2-hydroxypropionic acid with the chemical formula $C_3H_6O_3$. The salt form of lactic acid is referred to as "lactate" regardless of the neutralizing agent, e.g. calcium carbonate or ammonium hydroxide. As referred to herein, lactic acid can refer to either stereoisomeric form of lactic acid (L-lactic acid or D-lactic acid). The term lactate can also refer to either stereoisomeric form of lactate (L-lactate or D-lactate). When referring to lactic acid production this includes the production of either a single stereoisomer of lactic acid or lactate or a mixture of both stereoisomers of lactic acid or lactate.

As used herein, the term "fermentable carbohydrates" refers to carbohydrates which can be fermented by an organic acid producing microorganism. Generally, fermentable carbohydrates are $C_5$ sugars, $C_6$ sugars, oligomers thereof (e.g. dimeric $C_{12}$ sugars) and/or polymers thereof. By $C_5$ sugars and $C_6$ sugars is meant saccharides with 5 and 6 carbon atoms, respectively, and by $C_{12}$ sugars is meant saccharides with 12 carbon atoms (e.g. a disaccharide).

The carbohydrates that a specific microorganism can ferment are either commonly known to the person of ordinary skill in the art or are easily accessible in the published, background literature. For completeness, common carbohydrates fermentable by lactic acid producing microorganisms include but are not limited to: $C_5$ sugars such as arabinose, xylose and ribose; $C_6$ sugars such as glucose, fructose, galactose, rhamnose and mannose; and, $C_{12}$ sugars such as sucrose, maltose and isomaltose.

The content of fermentable carbohydrates in biomass may be determined by methods known in the art. A particularly instructive disclosure is Milne et al., *Sourcebook of Methods of Analysis for Biomass Conversion and Biomass Conversion Processes*. SERI/SP-220-3548. Golden, Colo.: Solar Energy Research Institute, February 1990.

As used herein the term "simultaneous saccharification and fermentation" is intended to mean the simultaneous enzymatic hydrolysis of oligomeric and polymeric carbohydrates of the pre-treated lignocellulosic material into fermentable saccharides together with the further conversion of saccharides into the fermentation product by one or more microorganism(s).

Caustic Magnesium Salt

The caustic magnesium salt of the present invention comprises one or more compounds selected from the group consisting of magnesium oxide (MgO), magnesium hydroxide ($Mg(OH)_2$), magnesium carbonate ($MgCO_3$), magnesium hydrocarbonate ($Mg(HCO_3)O_2$), alkaline magnesium silicate, trimagnesium phosphate, and mono-magnesium phosphate. Preferably, the caustic magnesium salt is selected from the group consisting of MgO, $Mg(OH)_2$, $MgCO_3$, $Mg(HCO_3)_2$ and mixtures thereof. More preferably, the caustic magnesium salt comprises or consists of MgO and/or $Mg(OH)_2$, The caustic magnesium salt may be provided, where applicable, in an aqueous solution. However, the caustic magnesium salts may equally provided in either their solid, particulate form or as an aqueous dispersion thereof.

Provision of the Lignocellulosic Material

The feedstock for the process of the present invention is a lignocellulosic material which broadly includes any material containing cellulose, hemicellulose and lignin, such as may be derived from plant biomass. It is preferred that the lignocellulosic feedstocks be characterized by a cellulose content of from 20 or 30 wt. % to 70 wt. %, based on the dry weight of the material and/or a combined cellulose and hemicellulose content of from 30 to 99 wt. %, preferably 35 to 95 wt. % based on the dry weight of the material.

Exemplary but non-limiting lignocellulosic materials include: jatropha; rapeseed; grasses, in particular $C_4$ grasses such as switch grass, cord grass, rye grass, miscanthus, reed canary grass and combinations thereof; palm fronds; sugar processing residues, including bagasse and beet pulp; agricultural residues, including in particular rice hulls, rice straw, corn, corn fiber, corn cobs, corn stover, wheat, wheat straw, maize, maize stover, sorghum, sorghum stover, sweet sorghum, sweet sorghum stover, soybean stover, barley straw, canola straw, oat straw and oat hulls; forestry biomass such as recycled wood pulp fiber, sawdust, timber, hardwood, softwood, and combinations thereof; and, cellulosic waste materials such as waste paper, newsprint, cardboard, paper pulp, paper mill residue and the like.

Preferred lignocellulosic materials are selected from the group consisting of: wheat straw; sugarcane bagasse; corn stover; and, mixtures thereof.

The lignocellulosic feedstock may comprise particles, fibers or other residues of one material alone or, alternatively, may originate from a plurality of different materials. It is also envisaged that the lignocellulosic feedstock be fresh, partially dried or fully dried. In certain circumstances it may be advantageous to use fresh lignocellulosic material; the natural or bound water content of that material can reduce or obviate the need to add water in forming the pre-treatment reaction mixture of the present invention.

The physical pre-treatment of lignocellulosic materials—which may precede, be combined with or be integrated with the recited pre-treatment with the caustic magnesium salt—is not precluded by the present invention. For instance, the lignocellulosic materials may be subjected to steam injection, torrefaction, pyrolysis or γ-irradiation. More usually, the materials may be subjected to mechanical comminution by one or more of shredding, chipping, grinding, compression/expansion, extrusion and milling, including vibratory ball milling: these processes may serve to: reduce the particle size of the lignocellulosic materials; increase the surface area of the material and its accessibility to hydrolytic enzymes; and, reduce cellulose crystallinity.

In an embodiment, the lignocellulosic material may either possess or be comminuted to a particle size of from 0.1 to 250 mm and preferably from 0.1 to 50 mm. Grinding may for instance be used to reduce the average particle size of the materials to from 10-30 mm; milling may achieve yet smaller particle sizes, having an average size of from 0.1 to 2 mm for instance. The desirable particle size distribution or comminution ratio of the lignocellulose materials depends in part on determining an acceptable energy consumption of the mechanical comminution step based on the predicted yield of lactic acid. The teaching of Cadoche, L. et al. *Assessment of size reduction as a preliminary step in the production of ethanol from lignocellulosic wastes* Biol. Wastes 1989, 30, 153-157 may be instructive in evaluating energy consumption for the size reduction of hardwoods and agricultural wastes as a function of final particle size and comminution ratio.

In an embodiment of the invention, the optionally physically pre-treated lignocellulosic material, is subjected to a pre-extraction step. As used herein, the term "pre-extraction" refers to any process or technique which is applied prior to the defined pre-treatment step with the intent of removing soluble components from the lignocellulosic biomass. Whilst such pre-extraction will generally be applied to remove non-fermentable, soluble components contained in the biomass, such as proteins, amino acids and soluble inorganic components, it is also envisaged that pre-extraction may be employed to remove soluble, fermentable components from the biomass.

In a still further embodiment of the invention, a step of acid hydrolysis may precede the contacting of the lignocellulosic material with the caustic magnesium salt, whereby the caustic salt may act to neutralize at least part of the acid present. Such an acid hydrolysis step is generally effected by contacting the feedstock with an acidic aqueous solution stream which may include one or more of an inorganic acid, an organic acid, an amino acid, a mineral acid, a Bronsted acid and a Lewis acid. More usually, the acid may be sulfuric acid, sulfonic acid, phosphoric acid, nitric acid, acetic acid, lactic acid, formic acid, oxalic acid, succinic acid, levulinic acid, carbonic acid, glycolic acid, uronic acid, glucaric acid, hydrofluoric acid, hydrochloric acid, boric acid, boron trifluoride, or any combination of these acids. Solutions containing acidic salts, such as aluminum sulfate, ferric sulfate, aluminum nitrate or ferric nitrate may also be useful.

Whilst concentrated acids may be powerful agents for cellulose hydrolysis, they are concomitantly toxic, corrosive and hazardous, and are therefore not preferred for use herein. Desirably therefore, when used, an aqueous acidic, pre-treatment solution should have a concentration of less than 8 wt. %, for instance less than 4 wt. %. A dilute acid pre-treatment step may typically occur at a temperature of from 120° C. to 230° C., such as from 150 to 200° C.

The person of ordinary skill in the art will of course be able to determine an appropriate contact or residence time, acid concentration and contact temperature for particular acids and ligncellulosic feedstocks. And the following teachings may inter alia be instructive in this regard: Esteghlalian, A. et al. *Modeling and optimization of the dilute-sulfuric-acid pretreatment of corn stover, poplar and switchgrass*, Bioresour. Technol. 1997, 59, 129-136. (77); Hinman, N. D. et al. *Preliminary estimate of the cost of ethanol production for SSF technology*, Appl. Biochem. Biotechnol. 1992, 34/35, 639-649; and, Brennan, A. H. et al. *High temperature acid hydrolysis of biomass using an engineering-scale plug flow reactor: Result of low solids testing*, Biotechnol. Bioeng. Symp. 1986, 17, 53-70.

Treatment with Caustic Magnesium Salt

In accordance with the process of the present invention, the lignocellulosic material, optionally treated as described hereinabove, is combined with the alkaline agent in the presence of water to form a reaction mixture.

The amount of alkaline agent so combined is determined such that the concentration of the caustic magnesium salt in the reaction mixture or slurry is at least 0.1 wt. % (w/w), preferably at least 0.5 wt. % (w/w), based on the dry weight of the lignocellulosic material. Typically, the amount of alkaline agent is determined such that the concentration of the caustic magnesium salt is at most 50 wt. % (w/w), based on the dry weight of the lignocellulosic material. Good results have, for instance, been obtained when the concentration of the caustic magnesium salt in the pre-treatment reaction mixture is from 0.5 to 40% (w/w) and particularly from 5 to 30% (w/w).

The reaction mixture or slurry formed should typically have a solids content of from 1 to 70% (w/w), for example from 10 to 60% (w/w) and preferably from 20 to 50% (w/w). The reaction mixture or slurry may be further characterized by a pH of from 8.0 to 14.0, preferably from 8.5 to 13.0 and more preferably from 9.0 to 12.0. As would be recognized by a person of ordinary skill in the art, a pH greater than 9 may be achieved by adding one or more caustic salts, other than the caustic magnesium salt(s) to the reaction mixture or slurry.

These characteristics of magnesium salt concentration, solids content and pH of the reaction mixture or slurry are not mutually exclusive; the mixture may possess any combination of the defined properties. A person of skill in the art will also recognize that the amounts of water and salt are result effective variables and thus the most preferred amounts thereof might differ from those values stated depending on the type of lignocellulosic material.

As previously noted, the alkaline agent may be added in a solid, particulate form before or after any water which is required to adjust the solids content to an appropriate level. Alternatively, the alkaline agent may be added as an aqueous solution or dispersion but this variant does not preclude the further addition of either water or particulate, solid alkaline agent to the mixture.

In an important embodiment of the present invention, the alkaline agent in the form a solid, aqueous solution or aqueous suspension is provided at a temperature above 25° C. for mixing with the lignocellulosic biomass; temperatures of from 25° C. to 300° C., or from 100° C. to 250° C. are feasible. This embodiment enables the caustic magnesium salt(s) to be sourced from thermal processes performed in situ without intermediate loss of thermal energy. By way of example, magnesium oxide sourced from in situ calcination may be utilized in this manner.

Suitable reactors or reaction vessels within which the reaction mixture may be disposed should be closed and pressurizable but preferably allow for any carbon dioxide formed during the reaction to be vented, either continuously or periodically. A person of ordinary skill in the art will be able to make an appropriate determination of a suitable reactor—or a suitable series of reactors—based on whether the reaction is to be performed as a batch process or an essentially continuous process with continuous feeding of reaction mixture and withdrawal of the hydrolysis product. Without intention to limit the present invention, examples of suitable reactors include: horizontal reactors with screw transport of the biomass; vertical tower reactors such as those disclosed, for example, in UK Patent Nos. GB 706,686 and GB 812,832.

In both batch and continuous processes, it is of course necessary to adequately mix the water, caustic salt and lignocellulosic material. It may also be desirable to cause mixing of the liquid phase, containing the lignocellulosic material, and any gas phase per se which may be present in the reactor. Adequate mixing may be achieved by, for instance, mechanical stirring, liquid phase recirculation or by selecting an appropriate flow rate through a tubular reactor.

Heat may be supplied to the reaction mixture by any suitable method including but not limited to: steam heating; induction heating; microwave heating; immersion of the reactor or reaction vessel in an appropriate heating bath; by means of a thermally conductive material which either contacts the reactor or reaction vessel or is immersed within the mixture and through which heated fluid is passed; or, similarly, by means of one or more electrical resistance heating elements contacting the outside of the reactor or reaction vessel and/or being immersed in the reaction medium. The reactor(s) or reaction vessels may optionally be pre-warmed prior to the introduction of the lignocellulosic material.

In an important embodiment of the present invention, the aqueous salt/biomass reaction mixture is maintained in the reaction vessel(s) at a temperature of from 130° C. to 250° C., such as from 140° C. or from 170° C. to 250° C., and preferably from 170° C. to 230° C. The reaction mixture should be at a pressure within the vessel(s) such that boiling of the liquid, aqueous medium does not occur under the temperature conditions in question. The total residence time in the reactor(s) at the above recited temperature and, as defined for the solids present within the reaction mixture, should be from 1 to 600 minutes, and more usually be from 1 to 480 minutes. As will be recognized, the residence time of the water within the reactor(s) may differ from that of the solids, depending on the type of reactor employed.

The preferred residence time will depend significantly upon the selected temperature, pH and type of lignocellulosic material. Selecting a higher temperature within the defined range can reduce the required residence time to achieve an effective hydrolysis. Analogously, operating at a higher pH within the recited range will also permit a reduced residence time.

By way of illustration good results have been obtained where the reaction mixture has a concentration of caustic magnesium salt of from 5 to 25% (w/w) and a pH of from 9.0 to 12, and said solids are held at a temperature of from 130° C. to 250° C. for a time period of from 1 minute to 240 minutes, preferably 1 to 30 minutes. Similarly, independent of the pH, good results have been obtained the reaction mixture has a concentration of caustic magnesium salt of from 5 to 25% (w/w) and where said solids of the reaction mixture are held a temperature of: either i) from 170° to 230° C. for a period of from 1 to 240 minutes, preferably from 1 to 120 minutes; or ii) from 140° to 170° C. for a period of from 180 to 600 minutes, preferably from 240 to 480 minutes.

In that embodiment of the invention where the lignocellulosic material has been previously subjected an acid hydrolysis step—an acid pre-treatment, optionally at elevated temperatures—and whereby the alkaline treatment a) is performed as a neutralization step, the temperature of that treatment step a) need not be as high as 130° C. For instance, the temperature may be from 15 to 100° C., in particular from 30 to 80° C. or from 45 to 70° C. An exemplary treatment of step a), in this context, is performed: i) at a pH of from 2 to 10, preferably from 4.0 to 9.0, more preferably from 4.5 to 8 and most preferably from 4.5 to 5.5; ii) at a temperature of from 15 to 100° C., preferably from 30 to 80° C.; and, iii) for a period of from 1 to 30 minutes, to neutralize the acid treated lignocellulosic material.

After the requisite residence time the product of the alkaline hydrolysis is collected for further processing.

Whilst it is not obligatory, the lignocellulosic feedstock may be processed, after the pre-treatment with caustic magnesium salt(s), to obtain a solids stream comprising the pre-treated feedstock and an aqueous stream comprising soluble components. This may be carried out by washing the pre-treated feedstock with an aqueous solution to produce a wash stream, and a solids stream comprising the pre-treated feedstock. Alternatively or additionally, the pre-treated feedstock may be subjected to a solids-liquid separation, using known methods such as centrifugation, microfiltration, plate and frame filtration, crossflow filtration, pressure filtration, vacuum filtration and the like. The aqueous stream thus obtained can itself be separately subjected to fermentation to ferment the available sugars: for example, xylose present in this stream may be fermented to ethanol, xylitol, lactic acid, butanol, or a mixture thereof.

The lignocellulosic material, pre-treated in the above described manner, is used as a substrate for digestion by enzymatic hydrolysis and microbial hydrolysis. Intermediate steps of acid hydrolysis and of wet oxidation, where the pre-treated material is contacted with oxygen at an elevated temperature of from 150 to 185° C., for instance, before enzymatic and/or microbial hydrolysis are not precluded by the present invention. Further, as is well-known in the art, the pH and temperature of the pre-treated lignocellulosic material or the solids stream comprising the lignocellulosic material may be moderated to facilitate enzymatic hydrolysis and/or microbial fermentation.

In preparation for biologically mediated transformation, the pre-treated lignocellulosic feedstock or the solids stream comprising the pre-treated feedstock is typically slurried in an aqueous solution such as process water, fresh water, steam condensate or process recycle streams. The aqueous slurry should ideally have a solids concentration that enables it to be pumped and the tolerated concentration of pretreated lignocellulosic feedstock in the slurry will then depend upon inter alia the particle size and water retention of the feedstock and the pump capacity.

In practice, the solids concentration is usually from 3 to 30 wt. %, based on the total weight of the slurry, with a solids concentration of from 10 to 25 wt. % being preferred. Where required, the concentration of suspended or undissolved solids can be determined by filtering a sample of the slurry using glass microfiber filter paper, washing the filter cake with water, and drying the cake overnight. It is further preferred that the fibrous or particulate solids comprise from 20 or from 30 wt. % to 70 wt. % cellulose.

In the process of the present invention, the pre-treated lignocellulosic material is processed by: saccharifying the treated aqueous lignocellulosic biomass in the presence of a hydrolytic enzyme to provide a saccharified aqueous lignocellulosic biomass comprising fermentable sugars and an insoluble lignocellulosic fraction; fermenting the saccharified aqueous lignocellulosic biomass in the presence of lactic acid forming microorganism and in the presence of a caustic magnesium salt to provide an aqueous fermentation broth comprising magnesium lactate and a solid lignocellulosic fraction; and, recovering magnesium lactate from the fermentation broth. Saccharification and fermentation steps are carried out simultaneously. The solid lignocellulosic fraction derived from the saccharification and fermentation steps comprises unhydrolyzed cellulose and hemicellulose and undissolved lignin fractions.

Saccharification generally uses one or more enzymes selected from the group consisting of: cellulases such as CBH1, CBH2, EG, and BGL; GH61 polypeptides having cellulolytic enhancing activity as described in, for example WO2005/074647, WO 2008/148131, and WO 2011/035027; hemicellulases; expansins; esterases, such as acetylxylan esterase (EC 3.1.1.72) that catalyzes the hydrolysis of acetyl groups from polymeric xylan, acetylated xylose, acetylated glucose, alpha-napthyl acetate, and p-nitrophenyl acetate; laccases; ligninolytic enzymes; pectinases; peroxidases; proteases; amylolytic accessory enzymes; inulinases, levanases; and, swollenins.

In one interesting embodiment of the invention, a pre-saccharification step of from 30 to 180 minutes performed at a temperature above 50° C., for instance 50 to 75° C., may precede the simultaneous saccharification and fermentation (SSF). Where such a pre-saccharification step is so-performed on the pre-treated lignocellulosic material, the teaching of the following documents may, by way of example be instructive: US 20130122554 (Honda Motor Co. Ltd) and Japanese Patent Laid Open Nos. 2006-101829 and 2008-271962.

The simultaneous saccharification and fermentation of the lignocellulosic material—hereinafter the fermentation medium—will now be described in more detail.

Simultaneous Saccharification and Fermentation

As is known in the art, the fermentation medium may be provided with additional fermentable carbohydrates. This may be necessary if the content of fermentable carbohydrates, as measured by high-pH anion exchange chromatography based on a calibration against appropriate C5, C6 and/or C12 sugar standards, is considered to be too low. It is also possible to combine a primary slurry having a relatively low fermentable carbohydrate content with a secondary slurry having a relatively high fermentable carbohydrate content.

It is also known to supplement the fermentation medium with additional nutrients besides the lignocellulosic material. Such additional nutrients, which may be added in solid form or as solutions or dispersions in water, typically comprise one or more of: mineral salts, in particular sources of mineral nitrogen, phosphate, sulfur and trace elements such as zinc, magnesium, calcium, manganese, potassium, sodium, boric, iron, cobalt, copper, molybdenum, nickel and aluminum; organic nitrogen, for example yeast autolysates and hydrolysates, plant protein hydrolysates, and, animal protein hydrolysates. Such organic nitrogen sources generally provide nitrogen in the form of free amino acids, oligopeptides, peptides, vitamins and traces of enzyme cofactors; the addition of such species to the medium in pure form is also not precluded.

During fermentation, carbohydrate degrading enzymes, as previously mentioned, may be added to the fermentation broth to assist the degradation of fermentable carbohydrates, especially those in polymeric form. This concept of simultaneous saccharification and fermentation is described in, for example, WO 03/095659 and US2013236933 (Huang et al.).

Prior to inoculation, the pH of the fermentation medium should be adjusted to a pH suitable for fermentation with the microorganism of choice. By adding an appropriate compound—usually an acid such as sulfuric acid, nitric acid, hydrochloric acid or, preferably, lactic acid—to the fermentation medium, the pH thereof is adjusted to a value of, usually, from 2 to 10. For illustration, pH values of the medium are typically from 5 or from 6 to 8 for simultaneous saccharification and fermentation, and are typically from 2 to 5 for so-called low pH fermentations. Where the lignocellulosic material was subjected to acid hydrolysis prior to being mixed and treated with the caustic magnesium salt, the neutralization of acid with that salt may, at this stage, mitigate the amount of the pH adjustant required to bring the pH to a desirable level.

In an interesting embodiment, the pH of the fermentation medium may be adjusted by the addition of an amount of lignocellulosic material which itself has an acidic pH on account of being treated by acid hydrolysis, such as described hereinabove.

The fermentation medium is fermented by means of a lactic acid producing microorganism—bacteria, yeasts and/or fungi, for instance—in the presence of a caustic magnesium salt to provide a fermentation broth containing magnesium lactate. The fermentation is generally performed by incubating the fermentation medium with the microorganism at a suitable temperature for a suitable period of time.

Suitable lactic acid producing microorganisms may include bacteria, fungi and yeasts, and may be selected from microorganisms that are either homolactic lactic acid producers or heterofermentative microorganisms which produce lactic acid. The microorganisms may be genetically engineered to produce or overproduce lactic acid.

Examples of such microorganisms include, but are not limited to: bacterial species of the genera *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus, Weissella, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*), *Caldicellulosiruptor* (including *Caldicellulosiruptor saccharolyticus*), *Clostridium* (including *Clostridium thermocellum*), *Thermoanaerobacterium* (including *Thermoanaerobacterium saccharolyticum*), *Ther-* moanaerobacter and Escherichia (including Escherichia coli); and, fungal and yeast species from the genera Saccharomyces (including Saccharomyes cerevisiae), Kluyveromyces (including Kluyveromyces lactis and Kluyveromyces marxianus), Issatchenkia (including Issatchenkia orientalis), Pichia(including Pichia stipitis), Candida (including Candida boidinii, Candida magnolia, Candida methanosorbosa, Candida sonorensis and Candida utilis) and Rhizopus (including Rhizopus arrhizus, Rhizopus microspores and Rhizopus oryzae).

Bacterial genera that are of particular interest are Lactobacillus, Bacillus (including Bacillus coagulans, Bacillus licheniformis, Bacillus smithii, Bacillus thermolactis and Bacillus thermoamylovorans), Geobacillus (including Geobacillus stearothermophilus and Geobacillus thermoglucosidans) and Escherichia (including Escherichia coli). Additionally or alternatively, preferred bacterial species are those that display optimal growth at a pH in the range of about 6 to about 8.

The incubation temperature may depend on the microorganism used. For example, the optimum temperature to be used may be established by analyzing the activity of the fermentation microorganism under different temperature conditions. In general, the temperature may be within the range from 30 to 80° C.; preferably a temperature with the range from 40 to 75° C. is used and more preferably a temperature of from 45 to 70° C.

As is known in the art, the pH of the fermentation medium may be adjusted and controlled during the fermentation: a drop in pH below a critical value, depending upon the microorganism used in the process, could damage the metabolic process of the microorganism and bring the fermentation process to a stop. Generally, the pH is adjusted during fermentation so as to maintained with the aforementioned ranges of from 4 to 9 or, preferentially, from 5 to 8.

Herein the adjustment of pH is effected by a caustic magnesium salt preferably selected from MgO, $Mg(OH)_2$, $MgCO_3$, $Mg(HCO_3)_2$ and mixtures thereof: the caustic magnesium salt neutralizes the lactic acid excreted by the microorganisms during fermentation, thereby generating a magnesium lactate salt. Optionally, a portion of the caustic magnesium salt present during fermentation may have been provided by or be residual from the pre-treatment step. Additionally or alternatively, the caustic magnesium salt may be purposively added during the course of fermentation. The addition of minor, supplementary amounts of other caustic salts, in particular caustic salts of alkali and alkaline earth metals is not precluded.

The person of ordinary skill in the art will be aware that magnesium lactate crystals can form during fermentation where the concentration of the salt is sufficiently high. Whether or not precipitation of magnesium lactate occurs will thereby depend on the concentration of fermentable carbohydrates in the fermentation medium, the fermentation temperature, the concentration of other constituents of the fermentation medium and the dilution factor of the added caustic magnesium salt. Typically, magnesium lactate remains soluble in a fermentation broth at a concentration of at the most 9.5 wt. % when measured at a temperature of 80° C.

The fermentation is allowed to proceed for a period of from 4 hours to 1 week; an exemplary period of from 8 hours to 3 days might be mentioned. The fermentation might equally be stopped when the content of fermentable carbohydrates in the liquid phase of the fermentation broth is below 5 g/l, for example below 2 g/l or 1 g/l. The amount of fermentable carbohydrates may be monitored by subjecting extracted samples of the fermentation broth to a solid/liquid separation step, thereby removing any solids from the liquid phase; a chromatogram of that liquid phase is then obtained by high-pH anion exchange chromatography using a suitable device such as a pulsed amperometric detector (HPAEC-PAD). The carbohydrate composition of the liquid phase is then determined based on a calibration performed by using appropriate standards (e.g. $C_5$, $C_6$ and/or $C_{12}$ sugar standards). Generally, the molar yield of lactic acid produced relative to the fermentable carbohydrates consumed (e.g. $C_5$, $C_6$ and/or $C_{12}$ sugars) is from 70 to 100%, in particular from 80 to 100%.

The fermentation of a fermentation medium comprising the pre-treated lignocellulosic material in combination with caustic magnesium salt can result in a fermentation broth comprising magnesium lactate in a concentration at which the magnesium lactate is only present in solution. However, it is preferred for crystallization of magnesium lactate to occur within the fermentation broth.

It is actually preferred in the present invention for the fermentation broth—comprising dissolved and crystalline magnesium lactate, the lignocellulosic fraction and biomass—to be recovered in toto and subjected to acidulation with hydrochloric acid either without prior treatment of the broth or after a concentration step whereby water is evaporated from the broth under ambient or reduced pressure to further crystallize out magnesium lactate.

There is no however intention in the present invention to limit the methods by which magnesium lactate may be concentrated and recovered from the fermentation broth. The term recovered is intended to encompass both isolation of magnesium lactate from the broth and the extraction of magnesium lactate as a solid, solution or suspension in combination with the biomass residue from the fermentation step. And one or more known or conventional methods of recovery like liquid/liquid extraction, nanofiltration, active carbon treatment, distillation and re-crystallization, adsorption, electro-dialysis, membrane separation, reactive extraction and esterification can be adopted herein. Further suitable methods are disclosed in inter alia WO2005/123647 and WO 2011/095631 (both Purac Biochem B.V.), the disclosures of which are incorporated herein by reference. And such methods may equally find utility in further purification steps applied to the magnesium lactate.

The present invention does not preclude methods of recovery of the magnesium lactate by which that salt is partially purified. For instance, in an exemplary method, the fermentation broth comprising dissolved and crystalline magnesium lactate is subjected to a solid/liquid separation; the solids thus obtained—which include magnesium lactate, lignin and biomass—are then further processed; and, the mother liquor may be recycled to a biologically mediated transformation process—to the enzymatic hydrolysis and/or the fermentation steps—to provide water balance thereto.

In an alternative partial purification method, dissolved magnesium lactate may be isolated from a fermentation broth by sequentially performing: i) a solid/liquid separation step, optionally conducted at a temperature of from 20 to 75° C. or from 30 to 60° C., by which the magnesium lactate-containing fermentation broth is treated by one or more of flotation, sedimentation, flocculation, centrifugation, filtration and decantation, to provide a magnesium lactate-containing medium which is separated from the biomass and other solid impurities which remain in the solid residue; and, ii) a concentration step to provide magnesium lactate crystals from the magnesium lactate medium. This concentration step ii) may be performed by removal of water under ambient or reduced pressure or by means of evaporative crystallization. Alternatively, this concentration step may be performed by evaporation followed by cooling crystallization. Salts originating from the lignocellulosic materials remain in the liquid phase and do not thereby co-precipitate or co-crystallize with the magnesium lactate crystals. The magnesium lactate crystals formed may be separated by solid/liquid separation and washed.

The recovered yield of lactic acid in the form of magnesium lactate crystals is usually from 50 wt. % or even from 70 wt. % to 99 wt. %, based on the amount of lactic acid produced during fermentation.

Acidulation of the Recovered Magnesium Lactate

After the recovery of magnesium lactate from the fermentation broth, an significant embodiment of the method of the present invention comprises the steps of: e) providing a feed comprising hydrogen chloride, said feed being either an aqueous solution comprising hydrogen chloride or a gas feed comprising gaseous hydrogen chloride; and, f) acidifying the recovered magnesium lactate to lactic acid by bringing said magnesium lactate into contact with said feed comprising hydrogen chloride, thereby forming a liquid effluent comprising lactic acid and magnesium chloride.

The acidulation is generally conducted using a molar excess of acid. That molar excess should however be small such that the liquid effluent obtained is not highly acidic, this being undesirable in view of the further processing of that effluent.

Furthermore, the acidulation is usually conducted at a temperature of from 20° C. to 150° C., such as from 40° C. to 120° C. and preferably from 45° C. to 80° C. At higher temperatures, it becomes uneconomical to adapt equipment to the harsh conditions of an acidic environment at high temperatures.

The magnesium lactate processed in step f) may be in the form of a solid, a solution, or a suspension. Whilst the last form is less usual, mixtures of lactic acid and magnesium lactate, as might be obtained in a low pH fermentation, can have this form and be subjected to acidulation.

In the preferred embodiment where the magnesium lactate is provided in solid form, the acidulation step f) is conducted by bringing the solid magnesium lactate into contact with an acidic HCl solution. That acidic solution should preferably have as high an acid concentration as possible to drive the formation of an aqueous mixture with a high carboxylic acid concentration. Desirably, the acidic aqueous solution should comprise at least 5 wt. %, preferably at least 10 wt. % and even more preferably at least 20 wt. % HCl, based on the total weight of the acidic solution. Under such processing conditions, a very high lactic acid concentration can be obtained; concentrations of from 15 to 50 wt. % might be mentioned.

Where the magnesium lactate is provided in dissolved form, usually as an aqueous solution, or in a dispersed form, the acidulation step f) can be conducted by bringing the magnesium lactate into contact either with an acidic solution of hydrogen chloride as described above or with an acidic gas comprising gaseous hydrogen chloride. In the latter case, the gas feed comprising gaseous HCl gas may be blown through the solution or suspension of the salt.

The gas feed provided to the acidification reaction generally comprises at least 1 wt. %, preferably at least 2 wt. %, more preferably at least 5 wt. % of hydrogen chloride, based on the total weight of the gas. A concentration of less than 1 wt. % is generally undesirable; in order to maintain an efficient acidification, such a low concentration would require a substantial architecture of pipes to feed the acidifying gas into the magnesium lactate solution or suspension liquid feed. Although high concentrations of hydrogen chloride in the gas feed are generally desirable, the gas feed will in practice comprise 20 wt. % or less of hydrogen chloride, based on the total weight of the gas.

Exemplary concentrations of gaseous HCl in the gas feed are from 5 to 15 wt. % or from 7 to 12 wt. %, based on the total weight of the gas. The HCl concentration of a gas obtained in the thermo-hydrolysis of magnesium chloride—as described hereinbelow—typically falls within one of these ranges.

In an embodiment of the present invention, the gas feed comprising gaseous hydrogen chloride further comprises gaseous water, wherein the hydrogen chloride to water weight ratio in the gas feed is between 1:10 and 10:1. In particular, the HCl/$H_2O$ weight ratio may be between 1:10 and 1:4, preferably between 1:6 and 1:4, and more preferably between 1:5 and 1:4.

Independently of this embodiment but preferably additionally, the gas feed comprising gaseous hydrogen chloride further comprises one or more inert gases. As used herein, the term "inert gas" as used herein refers to a gas that does not react, condense or absorb with the liquid feed during acidification and leaves the liquid feed as a gas after having been contacted with the liquid feed. Such inert gases are preferably selected from the group consisting of $N_2$, $O_2$, $CO_2$ and mixtures thereof. Whilst inert gases may constitute up to 95 wt. %, based on the total weight of the gas, amounts of from 40 to 80 wt. % of inert gas are more typical.

In the acidification of an aqueous solution or suspension of magnesium lactate with a gas feed comprising gaseous hydrogen chloride that is passed there-through, it is preferable to increase the temperature of that solution or suspension to from 60° to 120° C. before any contact with the gas feed. By so elevating the temperature, there is an enhanced selectivity for the adsorption of HCl from the gas stream as compared to the adsorption of water contained within that gas stream: this minimizes the dilution of the aqueous solution or suspension of magnesium lactate. Whilst the temperature of the gas feed is less critical in this context, it should not be so low that water present therein condenses as it passes through the solution or suspension of magnesium lactate.

The liquid effluent of the acidulation step f) may comprise solids materials such as lignin. Preferentially, such solid material is removed from the liquid effluent, by filtration for example, as its presence is not desirable during further processing steps, such as lactic acid extraction.

Lactic Acid Separation

There is no intention to limit the method by which the lactic acid may be separated from the liquid effluent of the acidulation step f) or from the optional separation step g). Conceivably, separation by extraction, solid adsorption, vaporization or membrane separation may be used, provided that said method also efficiently yields a magnesium chloride solution or suspension. In this regard, it is herein preferred that the separation step h) comprises the extraction of lactic acid.

Suitable methods of extraction of lactic acid from the liquid effluent product of the acidulation step f) or the optional separation step g) are taught in WO2013/093028 (Purac Biochem B.V.), the disclosure of which is incorporated herein by reference. Therein, the aqueous mixture—after the removal of solid material therefrom—is subjected to an extraction step by contacting it with an organic liquid comprising an organic solvent selected from the group of C5+ ketones, diethylether, and methyl-tertiary-butylether, thereby obtaining an organic lactic acid solution and an aqueous waste liquid comprising magnesium chloride. In this forward extraction, the lactic acid is separated from the impurities present in the aqueous mixture by dissolving it in the first organic liquid. The impurities will remain in the aqueous mixture.

It is acknowledged that the extraction methods of WO2013/093028 (Purac Biochem B.V.) are carried out on an aqueous medium comprising at least wt. % of magnesium chloride. If the product obtained from the acidulation step f) does not meet this requirement, various measures may be taken. For instance, magnesium chloride may be added to the product until the desired concentration is reached. Alternatively or additionally, a concentration step may be carried out to increase the concentration of magnesium chloride by removal of water. The aqueous mixture may be concentrated after acidulation but prior to extraction to a desired concentration up to the solubility of the magnesium chloride. During concentration, preferably no or substantially no precipitation of magnesium chloride should occur.

Alternative methods of the extraction of lactic acid from the product of the acidulation step f) are disclosed in: U.S. Pat. No. 6,509,179 B1 (Veldhuis-Stribos); and WO 00/17378 (IMI Institute for Research & Development). The disclosures of these documents are incorporated herein by reference.

The present invention does not preclude the purification of the extracted lactic acid using methodologies known the art. The teachings of the following documents may, by way of non-limiting examples be instructive in this regard: U.S. Pat. No. 6,630,603 (van Breugel et al.); Dutch Patent Application Nos. 1013265 and 1013682; Ullmans Encyklopädie der Technischen Chemie, Verlag Chemie GmbH, Weinheim, Fourth Edition, Volume 17, pp. 1-7 (1979); H. Benninnga "*History of Lactic Acid Making*", Kluwer Academic Publishers, Dordrecht-Boston-London (1990); C. H. Holten, "*Lactic Acid; Properties and Chemistry of Lactic Acid and Derivatives*", Verlag Chemie GmbH, Weinheim (1971); The Merck Index, Merck & Co., Inc., Eleventh Edition, p. 842 (1989); and, Rommp Chemie Lexicon, G. Thieme Verlag, Stuttgart and New York, Ninth Edition, Volume 4, pp. 2792-2893 (1991).

Thermo-Hydrolysis

In an important aspect of the invention, the process comprises the step of subjecting the aqueous waste liquid comprising magnesium chloride, as obtained in the separation or extraction step, to a thermal decomposition step at a temperatures of at least 300° C. Under these conditions, the chloride salt is thermally hydrolyzed yielding solid magnesium oxide and a gas comprising gaseous hydrogen chloride.

Preferably, thermal decomposition is conducted at a temperature of at least 350° C. Due to energy costs, the temperature is preferably below 1000° C., more preferably below 800° C., still more preferably below 600° C. In addition, using too high a temperature for the thermal decomposition step is undesirable because it will reduce the reactivity of the MgO formed, rendering it less suitable for use as a neutralizing agent in fermentation, for instance. In an exemplary embodiment, the temperature at which thermal decomposition is conducted may be 350-600° C. or 400-500° C. The temperature mentioned is the temperature of the gases as they are removed from the thermal hydrolysis unit.

The concentration of the magnesium chloride in the aqueous liquid to be thermally hydrolyzed should preferably be from 15 to 40 wt. %, and more preferably from 20 to 30 wt. %, based on the total weight of the aqueous liquid. Whilst they may be tolerable, lower $MgCl_2$ concentrations are not desirable on account of the high energy costs involved in evaporating water during thermo-hydrolysis.

Importantly, the solid magnesium oxide and gaseous hydrogen chloride products can be recycled to other stages in the recited process for lactic acid preparation: this can result in an overall process from which relatively little waste is produced. In particular, at least part of the magnesium oxide may be used directly in either step a) or step c) of the present invention. Alternatively, it may be used as a precursor for another caustic magnesium salt to be used in those steps. The formation of a magnesium hydroxide slurry, by bringing the magnesium oxide into contact with water, might be specifically mentioned in the latter regard. As the thermal decomposition step occurs at a high temperature, it does consume a substantial amount of energy. However, magnesium oxide recovered from the thermal decomposition step will be at an elevated temperature and heat may therefore be transferred from it to the aqueous media and/or lignocellulosic material of the pre-treatment step a) and the fermentation steps c). This can reduce the energy burden of those steps in a commercial process. Moreover, in step a), introducing solid magnesium oxide at an elevated temperature into a solid mass of lignocellulosic material, can facilitate the release of bound water from that material and may contribute to the breakdown of the lignin thereof.

At least part of the HCl derived from the thermal decomposition of magnesium chloride may be used to acidify the magnesium lactate obtained in the fermentation process. It is realistic that at least 80 mol. % of the HCl used in the acidulation step f) be derived from the thermal decomposition step; the derivation of at least 90 mol. % or at least 95 mol. % in this manner is not unusual.

At least two mechanisms for thermal energy conservation also exist through deriving HCl in this manner. An HCl gas stream derived from the thermal decomposition step may be subjected to a heat exchange step, wherein the temperature of the gas stream is decreased to a value in the range of 80-150° C.: a gas stream with this temperature can be provided directly to the acidification step f) and can further be transported thereto without requiring expensive thermal and corrosion resistant conduit materials. Analogously, the dissolution of the HCl derived at an elevated temperature from the thermal decomposition step can at least partially mitigate the thermal energy needed to heat an aqueous solution of the hydrogen chloride to the acidulation temperature.

It is noted the thermal decomposition product stream will generally contain gaseous water in addition to gaseous HCl. Whilst it is possible to remove water from the gas stream, such intermediate water removal is not essential: a gaseous stream comprising hydrogen chloride and water can be utilized in the acidification step, as noted above. The conduct of the thermo-hydrolysis in the presence of at least one inert gas will analogously yield a gas product stream comprising hydrogen chloride, said inert gas or gases and, generally water: such a gas stream can also be directly utilized in the acidulation step f). An illustrative gas feed for the acidulation step obtained in an $MgCl_2$ thermo-hydrolysis comprises 40-50 wt. % $N_2$, 0-5 wt. % $O_2$ and 5-15 wt. % $CO_2$.

The amount of water in the derived gas stream in a particular case will depend inter alia on the amount of water in the magnesium chloride solution and the amount of inert gas present during the thermal decomposition. In an exemplary embodiment, a gas feed obtained by thermo-hydrolysis of a 20-40 wt. % magnesium chloride solution will generally have a hydrogen chloride to water weight ratio ($HCl/H_2O$ ratio) that is at least 1:10 and at most 1:4. In case a magnesium chloride concentration of 25-30 wt. % is used, it will generally have an $HCl/H_2O$ ratio between 1:6 and 1:4, in particular between 1:5 and 1:4. In this case, the derived gas feed for the acidifying step f) typically comprises 5-15 wt. % HCl and 30-45 wt. % water. The person of ordinary skill in the art will be able to concentrate or dilute the derived gas feed where he desires to work with higher or lower HCl concentrations.

Whilst the industrial utility of lactic acid is well known, those impurities originating from the pre-extraction, pretreatment and/or fermentation steps of the present invention may also find utility after appropriate physical and/or chemical processing. It is envisaged that residual cellulose and lignin may serve as boiler fuel for electricity or steam production. Further, black liquor gasification of lignin is a recent commercial development. Certain impurities may be used as fertilizer, particularly magnesium rich fertilizer. And carbon dioxide released in the fermentation process may be captured for sale, for example, to the beverage industry.

The present invention is further illustrated by the following Example, without being limited thereto or thereby.

EXAMPLES

Raw Materials and Their Analysis:

Bagasse was provided by Purac Thailand Ltd. (Rayong, Thailand).

Ground wheat straw was obtained from a local supplier. For Examples 1 to 9 below, the wheat straw was milled using a Retch Cutting Mill (SM100) and then screened to attain a median particle size in the range from 500 microns to 1 mm. For Examples 10 to 12 below, the wheat straw was milled using hammer mill (Apex Commuting Mill) with a screen size of 1.5 mm.

Using a Mettler Toledo Advanced Moisture Analyzer, the dry weight contents of selected 0.5-2.0 g milled wheat straw samples shed—were measured.

The wheat straw and bagasse were analyzed for carbohydrate, acid soluble lignin, acid insoluble lignin and ash contents in accordance with the procedure given in: *Determination of Structural Carbohydrates and Lignin in Biomass: Laboratory Analytical Procedure* (*LAP*), National Renewable Energy Authority (August 2012) http://www.nrel.gov/docs/gen/fy13/42618.pdf; and, Determination of Ash in Biomass: Laboratory Analytical Procedure (LAP), National Renewable Energy Authority (January 2008) http://www.nrel.gov/docs/gen/fy08/42622.pdf. Where applicable, current practice relating to said procedures may be found at htt://www.nrel.gov/biomass/analytical_procedures.html.

Where applicable, glucose was determined using the Megazyme D-Glucose assay kit (glucose oxidase/peroxidase; GOPOD) employing a pulsed amperometric detector (Roche/Hitachi GOD-PAD) and spectrophotometry (Hitachi U-2800, 540 nm). Xylose may be determined using the Megazyme D-xylose kit and spectrophotometry (Hitachi U-2800, 340 nm).

The theoretical maximum yield of glucose from wheat straw was determined to be 37.1 wt. %, based on the total dry weight.

Examples 1-9

Pre-Treatment:

Weighed 12.45 g portions of the milled wheat straw or bagasse were separately slurried in 150 ml demineralised water, following which the solid magnesium oxide or, where applicable, solid calcium oxide or sodium hydroxide were added thereto; no further basic compounds were added. For completeness, it is noted that in Example 9 below, the NaOH was added to the milled wheat straw after the solid magnesium oxide, thereby raising the pH of that sample.

The pre-treatment of said samples was carried out in a double wall stainless steel, stirred reactor (Buchi Autoclave). The reactor was rated for 60 Bar and was equipped with a pressure safety spring. Heating was carried out using hot oil up to 190° C.

The properties of each separate portion and the different conditions of temperature and residence time to which they were subjected are shown in Table 1 herein-below. All samples were continuously stirred for the requisite residence time in the reactor. Further all samples that were treated with caustic magnesium or calcium oxide had an initial pH of from 8.5-9.4 prior to any heating step.

Preparation for Enzymatic Hydrolysis:

The thus pre-treated solids were subjected to a first solid/liquid separation step using a Buchner filter under reduced pressure (approx. 200 mBar). The liquid fraction was collected for analysis. The solids were collected, dispersed in water and neutralized to a pH of from 6-7 with lactic acid.

Next the solids were subjected to a two-stage second solid/liquid separation step using a filtering centrifuge (Hermle Sieva 2) equipped with a 5 micron filter cloth. In a first stage, the centrifuge is initiated at 5000 rpm before being increased to 10000 rpm; the filtrate is collected and added to the centrifuge again; samples of the then derived filtrate and filter cake are collected for analysis. In a second stage, the centrifuge is re-initiated with the addition of 1 liter of demineralized water thereto. The separated solid fraction was then collected; its dry matter content was measured before being subjected to enzymatic hydrolysis.

Enzymatic Hydrolysis:

At a dry matter content of 10% (w/w), the pre-treated solids were hydrolyzed in 50 mL polypropylene tubes with a cellulase enzyme mix CMAX4 available from Dyadic. A potassium phosphate buffer (pH, 6.4) was employed and, furthermore, sodium azide (0.02%, w/w) was present to prevent microbial infection of the hydrolyzate. The added amount of enzyme was varied in the experiments—as indicated in Table 1—with enzyme loading of 20 mg/g dry weight being more usual, noting that this loading should ensure satisfactory release of carbohydrates (NREL, 2011).

The hydrolyzation reactions were incubated at 52° C. at 300 rpm. After 24 hours, 48 hours and 72 hours, duplicate 0.2 ml samples were taken and filtered using a micro plate; the duplicate supernatants were then analyzed.

The concentrations of glucose are given in Table 1 below.

TABLE 1

| Example | Substrate | Pre-Washed (Y/N) | Treatment Temp. (° C.) | Residence Time (min.) | Alkaline Agent | Alkaline Agent Dosage (% w/w) | Enzyme dosage (mg protein/g dry solids) | Glucose concentration (g/L, at 72 h) |
|---|---|---|---|---|---|---|---|---|
| 1 | Milled Wheat straw | Y | 190 | 60 | MgO | 12 | 5 | 23.3 |
| 2 | Milled Wheat straw | Y | 190 | 120 | MgO | 12 | 5 | 14.9 |
| 3 | Milled Wheat straw | Y | 190 | 60 | MgO | 8 | 5 | 18.1 |

TABLE 1-continued

| Example | Substrate | Pre-Washed (Y/N) | Treatment Temp. (° C.) | Residence Time (min.) | Alkaline Agent | Alkaline Agent Dosage (% w/w) | Enzyme dosage (mg protein/g dry solids) | Glucose concentration (g/L, at 72 h) |
|---|---|---|---|---|---|---|---|---|
| 4 | Milled Wheat straw | Y | 190 | 120 | MgO | 8 | 5 | 13.0 |
| 5 | Milled Wheat straw | Y | 190 | 60 | MgO | 10 | 20 | 40.6 |
| 6 | Milled Wheat straw | N | 190 | 60 | MgO | 10 | 20 | 37.5 |
| 7 | Milled Wheat straw | Y | 190 | 30 | MgO | 10 | 20 | 37.2 |
| 8 (Comparative) | Milled Wheat straw | Y | 85 | 480 | CaO | 8 | 20 | 22.9 |
| 9 | Bagasse | Y | 190 | 20 | MgO + NaOH (pH = 11) | 10 | 20 | 13.7 |

It is clear from Table 1 that the elevated temperature pre-treatment of the wheat straw with caustic magnesium salt facilitates the subsequent hydrolysis of this biomass, as evidenced by the attained concentrations of glucose.

Example 10

This Example is intended to demonstrate the scaling up of the pre-treatment process to accommodate larger amounts of lignocellulosic material.

Pre-Treatment:

Weighed 1.6 kg portions of the milled wheat straw were separately slurried in 13.4 liters of demineralised water, following which the solid magnesium oxide was added thereto; no further basic compounds were added.

The pre-treatment of said samples was carried out in a double wall stainless steel, jacketed reactor equipped with an anchor propeller (50 liter Buchi Autoclave). The reactor was rated at greater than 20 Bar and was equipped with a pressure safety spring. Heating to 190° C. was carried out using both direct injection of pressurized steam and hot oil circulated through the jacket. The reaction mixture was stirred continuously during its residence time in the reactor.

After the reaction was performed, the reactor was cooled using oil circulated in the jacket followed by a rapid cooling effected by releasing the pressure of the reactor. The contents of the reactor were then collected.

The properties of the collected material and the conditions of temperature and residence time to which that material had been subjected are shown in Table 2 herein-below. Further the samples that were treated with caustic magnesium oxide in this manner had an initial pH of from 8.5-9.4 prior to any heating step.

Preparation for Enzymatic Hydrolysis:

The thus pre-treated solids were subjected to a first solid/liquid separation step under gravity using a 1 mm screen, the liquid fraction being collected in a 120 liter vessel. The solids were collected, dispersed in water in a further 120 liter vessel and neutralized to a pH of from 6-7 with lactic acid (50 wt. % aqueous solution).

The slurry formed was again filtered under gravity as described above (1 mm screen) except that 26 liters of demineralized water was sprinkled evenly over the filter cake. The filter cake was divided into six portions (SPs) each of which was pressed at an applied pressure of 250 Bar using a bench press filter (Fischer MachineFabriek). Each separated solid fraction was then collected; the cakes were subsequently broken up, homogenized and distributed over two containers (SP1, SP2). The dry matter content of each container was measured and found to be from 38-42% (w/w).

Enzymatic Hydrolysis:

The pre-treated solids were hydrolyzed in polypropylene tubes with a cellulase enzyme mix CMAX4 available from Dyadic; the pre-treated solids were added so as to be in an amount of 10 wt. %, by dry weight (c. 1 g dry weight). A potassium phosphate buffer (pH, 6.4) was employed and, furthermore, sodium azide (0.02%, w/w) was present to prevent microbial infection of the hydrolyzate. The enzyme loading was 20 mg/g dry weight.

The hydrolyzation reactions were incubated at 52° C. at 300 rpm. After 24 hours and 48 hours, duplicate 0.2 ml samples were taken and filtered using a micro plate; the duplicate supernatants were then analyzed.

The concentration of glucose are given in Table 2 below.

TABLE 2

| Example | Substrate | Treatment Temp. (° C.) | Residence Time (min.) | Alkaline Agent | Alkaline Agent Dosage (% w/w) | Enzyme dosage (mg protein/g dry solids) | Glucose concentration (g/L, at 48 h) |
|---|---|---|---|---|---|---|---|
| 10 | Milled Wheat straw | 190 | 59 | MgO | 10 | 20 | 53.2 |

Example 11

Pre-Treatment:

Weighed 1.6 kg portions of the milled wheat straw were pre-treated in an identical manner to that described for Example 10 above. The properties of the collected material and the conditions of temperature and residence time to which that material had been subjected are thus shown in Table 2 herein-above. Further, as previously the samples that were treated with caustic magnesium oxide in this manner had an initial pH of from 8.5-9.4 prior to any reactor heating step.

Preparation for Simultaneous Saccharification and Fermentation:

The thus pre-treated solids were subjected to a first solid/liquid separation step under gravity using a 1 mm screen, the liquid fraction being collected in a 120 liter vessel. The filter cake was divided into 11 portions (SSFPs) each of which was pressed at an applied pressure of 250 Bar using a bench press filter (Fischer MachineFabriek). Each separated solid fraction was then collected; the cakes were subsequently broken up, homogenized and distributed over two containers (SSF1, SSF2). An averaged dry matter content of each container was measured as: 40.26% w/w, SSF1; and, 42.95% w/w, SSF2.

Simultaneous Saccharification and Fermentation

As used in this Example, *Bacillus coagulans* DSM2314 is a publically available, non-GMO strain. A work stock of *Bacillus coagulans* DSM2314 was taken from a −80° C. freezer and pre-cultured in a sterile medium containing 7.7 g/l dextrose monohydrate, 2 g/l DAP, 3.5 g/l DAS, 1 g/l $CaCl_2 \cdot 5H_2O$, and 10 g/l yeast extract paste (50% Dry Solids).

Seed Fermentation:

To generate a seed fermentation, a standard Minifors unit was loaded with 1 liter of said sterile fermentation medium. To this medium was added 50 ml of the above inoculum. The medium was stirred at 200 rpm and maintained at a temperature of 52° C. for approximately 20 hours. The pH of the medium was also maintained at 6.4 during this period by the addition of magnesium hydroxide (aqueous solution) thereto.

Simultaneous Saccharification and Fermentation:

the simultaneous saccharification and fermentation was performed in a further minifors unit adapted to include a high torque, helical stirrer and an external 1 rpm pump for the addition of sludge to said unit.

In this Example, a two hour pre-saccharification step was employed, whereby the substrate (SSF1) was first loaded into the adapted minifors unit in the absence of the inoculum at a substrate loading of 5% (w/w) dry matter. The pre-saccharification was performed with cellulase enzyme mix CMAX4 (Dyadic) at an enzyme loading of 20 mg/g dry weight; at a start volume of 1300 ml, the pre-saccharification medium was stirred at 200 rpm and maintained at a temperature of 52° C. and a pH of 6-7.

After two hours, 100 ml of the inoculum was introduced and the reactor maintained at the above conditions of stirring, temperature and pH for a further 3 hours, again using magnesium hydroxide to control the pH.

Following this, the stirrer was stopped and first 50 g dosage of substrate (SSF1) introduced; the stirrer was then re-started to 200 rpm and the temperature of the reactor moderated to 52° C., if required. The pH was monitored and further 50 g dosages of substrate added in the same manner when the pH of the medium fell below 6.4. Such substrate addition was continued until the content of the reactor was approximately 20% (w/w) dry matter.

25 ml samples of the supernatant were taken regularly, on average every 3 hours and used to determine the concentration of glucose, xylose and lactic acid, lactic acid concentration being determined using HPLC. Measurements were stopped at 24.8 hours total time (pre-saccharification plus SSF time).

TABLE 3

| Ex. | Solid loading pre-saccharification | *Initial Glucose concentration (g/L) | *Initial Xylose concentration (g/L) | Total Fermentation/ SSF time (hours) | Final Lactic acid concentraation (g/L) |
| --- | --- | --- | --- | --- | --- |
| 11 | 5% wt | 17.8 | 7.3 | 24.8 | 99.6 |

*Concentration measured at the end of pre-saccharification

Figure 1:
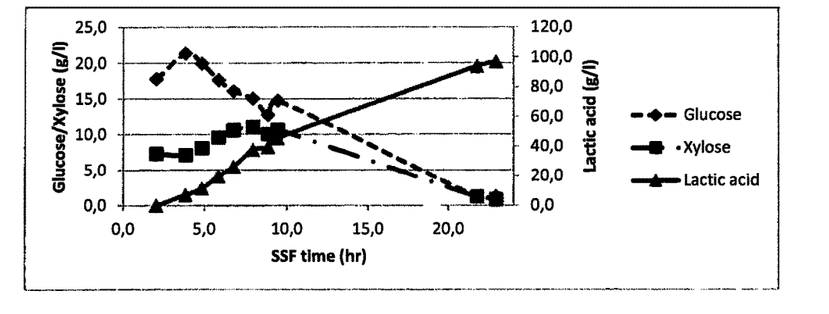

FIG. 1 appended hereto illustrates the change in concentration of glucose, xylose and lactic acid over time during the simultaneous saccharifcation and fermentation.

It will be apparent to those skilled in the art, upon consideration of the specification, that various modifications can be made in the disclosed embodiments without departing from the scope of the invention. It is therefore intended that the embodiments and examples be considered illustrative only, with the true scope of the invention being indicated by the following claims.

The invention claimed is:

1. A method for producing a fermentation product comprising lactic acid from lignocellulosic material, said method comprising:
   a) providing a lignocellulosic material and treating said material with an alkaline agent in the presence of water to provide a treated aqueous lignocellulosic material, said alkaline agent comprising a caustic magnesium salt, wherein the concentration of the caustic magnesium salt in the reaction mixture is from 5 to 30 wt. % based on the dry weight of the lignocellulosic material (w/w);
   b) saccharifying the treated aqueous lignocellulosic material in the presence of a hydrolytic enzyme to provide a saccharified aqueous lignocellulosic material comprising fermentable carbohydrate and a solid lignocellulosic fraction;
   c) fermenting the saccharified aqueous lignocellulosic material in the presence of a lactic acid forming microorganism and in the presence of a caustic magnesium salt to provide an aqueous fermentation broth comprising magnesium lactate and a solid lignocellulosic fraction; and,
   d) recovering lactic acid and/or a lactate salt from said aqueous fermentation broth, wherein the hydrolytic enzyme is selected from the group consisting of cellulases, GH61 polypeptides, hemicellulases, expansins, esterases, laccases, ligninolytic enzymes, pectinases, peroxidases, proteases, amylolytic accessory enzymes, inulinases, levanases, swollenins and mixtures thereof;

wherein the fermentable carbohydrates are C5 sugars, C6 sugars, oligomers thereof, polymers thereof, or combinations of the foregoing; and wherein said saccharification and said fermentation are carried out simultaneously.

2. The method according to claim 1, wherein the lignocellulosic material provided to step a) has been subjected to one or more of pre-extraction, steam pre-treatment, acid hydrolysis and mechanical comminution.

3. The method according to claim 1, wherein said lignocellulosic material provided to step a) is particulate and has an average particle size of from 0.1 to 250 mm.

4. The method according to claim 1, wherein step a) comprises:
i) providing a lignocellulosic material;
ii) mixing said lignocellulosic material with said alkaline agent in the presence of water to form a reaction mixture having a solids content; and,
iii) heating said reaction mixture such that said solids are held at a temperature of from 130° C. to 250° C. for a time period of from 1 minute to 600 minutes.

5. The method according to claim 4, wherein the total solids concentration of the reaction mixture is from 1 to 70% (w/w).

6. The method according to claim 4, wherein said reaction mixture has a pH of from 8.0 to 14.0.

7. The method according to claim 4, wherein:
the reaction mixture has a pH of from 9.0 to 12.0 and, in step iii), said solids are held at a temperature of from 130° C. to 250° C. for a time period of from 1 minute to 240 minutes.

8. The method according to claim 4, wherein:
the reaction mixture has a concentration of caustic magnesium salt of from 5 to 25% (w/w); and,
said solids of the reaction mixture are held at a temperature of from 140° to 170° C. for a period of from 180 to 600 minutes.

9. The method according to claim 4, wherein:
the reaction mixture has a concentration of caustic magnesium salt of from 5 to 25% (w/w); and,
said solids of the reaction mixture are held at a temperature of from 170° C. to 230° C. for a period of from 1 to 240 minutes.

10. The method according to claim 1 comprising subjecting the lignocellulosic material to acid treatment prior to treating said material with the alkaline agent of step a),
wherein said acid treatment comprises mixing said lignocellulosic material with an acidic aqueous solution having a concentration of 8 wt. % or less of acid selected from the group consisting of inorganic acid, organic acid, amino acid, mineral acid, Bronsted acid, Lewis acid and mixtures thereof, and
wherein said mixing takes place at a temperature of from 120° C. to 230° C.

11. The method according to claim 10, wherein the treatment of step a) is performed
i) at a pH of from 2 to 10;
ii) at a temperature of from 15 to 100° C.; and
iii) for a period of from 1 to 30 minutes,
to neutralize the acid treated lignocellulosic material.

12. The method according to claim 1, wherein the alkaline agent of step a) comprises or consists of a caustic magnesium salt selected from MgO, Mg(OH)$_2$, MgCO$_3$, Mg(HCO$_3$)$_2$ and mixtures thereof.

13. The method according to claim 12, wherein the caustic magnesium salt of step a) comprises at least one of MgO and Mg(OH)$_2$.

14. The method according to claim 1, wherein the caustic magnesium salt of step c) is selected from at least one of MgO, Mg(OH)$_2$, MgCO$_3$ and Mg(HCO$_3$)$_2$.

15. A method for producing a fermentation product comprising lactic acid from lignocellulosic material, said method comprising the steps of:
a) treating a lignocellulosic material with an alkaline agent in the presence of water to provide a treated aqueous lignocellulosic material, said alkaline agent comprising a caustic magnesium salt, wherein the concentration of the caustic magnesium salt in the reaction mixture is from 5 to 30 wt. % based on the dry weight of the lignocellulosic material (w/w);
b) saccharifying the treated aqueous lignocellulosic material in the presence of a hydrolytic enzyme to provide a saccharified aqueous lignocellulosic material comprising fermentable carbohydrate and a solid lignocellulosic fraction;
c) fermenting the saccharified aqueous lignocellulosic material in the presence of a lactic acid forming microorganism and in the presence of a caustic magnesium salt to provide an aqueous fermentation broth comprising magnesium lactate and a solid lignocellulosic fraction;
d) recovering magnesium lactate from said aqueous fermentation broth;
e) providing a feed comprising hydrogen chloride, said feed being either an aqueous solution comprising hydrogen chloride or a gas feed comprising gaseous hydrogen chloride; and,
f) acidifying the magnesium lactate to lactic acid by bringing said magnesium lactate into contact with said feed comprising hydrogen chloride, thereby forming a liquid effluent comprising lactic acid and magnesium chloride,
wherein the hydrolytic enzyme is selected from the group consisting of cellulases, GH61 polypeptides, hemicellulases, expansins, esterases, laccases, ligninolytic enzymes, pectinases, peroxidases, proteases, amylolytic accessory enzymes, inulinases, levanases, swollenins and mixtures thereof;
wherein the fermentable carbohydrates are C5 sugars, C6 sugars, oligomers thereof, polymers thereof, or combinations of the foregoing; and
wherein said saccharification and said fermentation are carried out simultaneously.

16. The method according to claim 15, further comprising:
g) separation of lignin from the liquid effluent product of step f).

17. The method according to claim 15, further comprising:
g) separation of lignin from the liquid effluent product of step f); and,
h) separation of the lactic acid and magnesium chloride present in the liquid effluent product of step g) to obtain a lactic acid product stream and a magnesium chloride solution or suspension.

18. The method according to claim 17, wherein the separation step h) comprises a lactic acid extraction step.

19. The method according to claim 17, wherein the separated magnesium chloride solution or suspension is subjected to a temperature of at least 300° C., thereby decomposing magnesium chloride into magnesium oxide and hydrogen chloride and thus obtaining a solid comprising magnesium oxide and a gas comprising gaseous hydrogen chloride.

20. The method according to claim 19, wherein said magnesium oxide derived from said step of thermally decomposing magnesium chloride is used directly in at least one of step a) and step c) or, alternatively, is used as a precursor for a caustic magnesium salt used in at least one of step a) and step c).

21. The method according to claim 20, wherein heat conserved in the solid magnesium oxide from the thermal decomposition of magnesium chloride is transferred to the lignocellulosic material of step a) and/or the fermentation broth of step c).

22. The method according to claim 19, wherein said feed comprising hydrogen chloride as used in step e) is at least partially derived from gaseous hydrogen chloride obtained from the thermal decomposition of the magnesium chloride.

23. The method according to claim 15 wherein the magnesium lactate as recovered in step d) is at least partially in crystalline form.

24. The method process according to claim 15 wherein said feed comprising hydrogen chloride is an acidic aqueous solution in which the concentration of hydrogen chloride is at least 5 wt. %, based on the total weight of the acidic solution.

25. The method according to claim 18, wherein the extracted lactic acid is subjected to a purification step.

\* \* \* \* \*